(12) United States Patent
Katsuhara

(10) Patent No.: US 10,297,131 B2
(45) Date of Patent: May 21, 2019

(54) PROVIDING SAFE MOBILITY WHILE DETECTING DROWSINESS

(71) Applicant: Toyota Motor Engineering & Manufacturing North America, Inc., Erlanger, KY (US)

(72) Inventor: Yasuo Katsuhara, Mountain View, CA (US)

(73) Assignee: TOYOTA MOTOR ENGINEERING & MANUFACTURING NORTH AMERICA, INC., Plano, TX (US)

( * ) Notice: Subject to any disclaimer, the term of this patent is extended or adjusted under 35 U.S.C. 154(b) by 0 days.

(21) Appl. No.: 15/627,288

(22) Filed: Jun. 19, 2017

(65) Prior Publication Data

US 2018/0365961 A1 Dec. 20, 2018

(51) Int. Cl.
| | |
|---|---|
| G08B 21/06 | (2006.01) |
| G08B 23/00 | (2006.01) |
| A61B 5/16 | (2006.01) |
| A61B 5/024 | (2006.01) |

(52) U.S. Cl.
CPC .......... *G08B 21/06* (2013.01); *A61B 5/02438* (2013.01); *A61B 5/16* (2013.01)

(58) Field of Classification Search
None
See application file for complete search history.

(56) References Cited

U.S. PATENT DOCUMENTS

| | | |
|---|---|---|
| 5,712,618 A | 1/1998 | McKenna |
| 6,822,573 B2 | 11/2004 | Basir et al. |
| 6,870,478 B2 | 3/2005 | Yasushi et al. |
| 7,397,382 B2 | 7/2008 | Ikegami et al. |
| 8,725,311 B1 | 5/2014 | Breed |
| 8,902,070 B2 | 12/2014 | Kobetski et al. |
| 9,135,803 B1 | 9/2015 | Fields et al. |
| 9,460,601 B2 | 10/2016 | Mimar |
| 9,792,801 B2 * | 10/2017 | Savolainen ............ B60K 28/02 |

(Continued)

OTHER PUBLICATIONS

E. Vural et al.; "*Automated drowsiness Detection for Improved Driving Safety*"; University of California San Diego Institute of Neural Computation, La Jolla, San Diego; (15 pages).

(Continued)

*Primary Examiner* — John F Mortell
(74) *Attorney, Agent, or Firm* — Snell & Wilmer LLP

(57) ABSTRACT

Methods, systems, and apparatus for a drowsiness detection system that alerts the user to potentially drowsiness. The drowsiness detection system includes a sensor configured to detect a heart rate of a user. The drowsiness detection system includes an indicator configured to alert the user before the user becomes drowsy and a processor that is connected to the sensor and the indicator. The processor is configured to obtain the heart rate of the user and measure the heart rate of the user. The processor is configured to calculate at least one of a heart rate variability or a heart rate interval of the user based on the measured heart rate. The processor is configured to determine that the at least one of the heart rate variability or the heart rate interval of the user indicates that the user is becoming drowsy and activate the indicator to alert the user before the user becomes drowsy.

18 Claims, 5 Drawing Sheets

(56) References Cited

U.S. PATENT DOCUMENTS

| | | | |
|---|---|---|---|
| 2008/0071177 A1* | 3/2008 | Yanagidaira | A61B 5/024 600/483 |
| 2011/0193707 A1* | 8/2011 | Ngo | G08B 21/06 340/576 |
| 2015/0265164 A1* | 9/2015 | Gopalakrishnan | A61B 5/02405 600/301 |
| 2016/0046294 A1 | 2/2016 | Lee et al. | |
| 2016/0354026 A1 | 12/2016 | Zohar | |
| 2017/0181713 A1* | 6/2017 | Feng | A61B 5/7282 |

OTHER PUBLICATIONS

K. Brookhuis et al.; "The use of psychophysiology to assess driver status"; Ergonomics vol. 36, No. 9, 1993; pp. 1099-1110; (13 pages).

H. Shuyan et al.; "Driver drowsiness detection with eyelid related parameters by Support Vector Machine"; Expert Systems with Applications, vol. 36, Issue 4, 2009; pp. 7651-7658; (8 pages).

M. Yeo et al.; "Can SVM be used for automatic EEG detection of drowsiness during car driving?"; Safety Science, vol. 47, Issue 1, Jan. 2009; pp. 115-124; (10 pages).

Q. Ji et al.; "Real-Time Nonintrusive Monitoring and Prediction of Driver Fatigue"; IEEE Transactions on Vehicular Technology, vol. 53, No. 4, Jul. 2004; (17 pages).

\* cited by examiner

PROVIDING SAFE MOBILITY WHILE DETECTING DROWSINESS

BACKGROUND

1. Field

This specification relates to a system and a method for detecting drowsiness before a user becomes drowsy.

2. Description of the Related Art

Safe driving is a major concern of societies. Thousands of people are killed, or seriously injured due to drivers falling asleep or drowsiness at the wheel each year. Drowsiness or fatigue is a direct and contributing cause of road related accidents that endanger lives. Effective warning of symptoms of drowsiness allow for corrective actions to be taken to prevent disastrous outcomes. Different technologies measure movements of physiological features like heart rate, pulse rate, eyelid movement, and head movement to detect drowsiness. For example, some systems detect drowsiness by recognizing whether a driver's eyes are open or closed, and, if open, the degree of openness. In other examples, systems estimate the driver's fatigue level by monitoring eyelids and determining eye opening and blink rates. The systems, however, are reactive systems that detect driver fatigue when the symptoms of fatigue or drowsiness have already set in. That is, these systems do not detect drowsiness in a driver before the drowsiness becomes apparent through the operation of the vehicle or recognizable by the driver. Thus, these reactive systems are unable to detect drowsiness before a driver is drowsy.

Accordingly, there is a need for a system and method for predicting a user's drowsiness and alerting the user before the user becomes drowsy.

SUMMARY

In general, one aspect of the subject matter described in this specification is embodied in a drowsiness detection system. The drowsiness detection system includes a sensor configured to detect a heart rate of a user. The drowsiness detection system includes an indicator configured to alert the user before the user becomes drowsy and a processor that is connected to the sensor and the indicator. The processor is configured to obtain the heart rate of the user and measure the heart rate of the user. The processor is configured to calculate at least one of heart rate variability or a heart rate interval of the user based on the measured heart rate. The processor is configured to determine that the at least one of the heart rate variability or the heart rate interval of the user indicates that the user is becoming drowsy and activate the indicator to alert the user before the user becomes drowsy.

These and other embodiments may optionally include one or more of the following features. The drowsiness detection system may include a memory for storing a baseline heart rate of the user, and the processor may be configured to compare the stored baseline heart rate with the detected heart rate of the user to determine that the at least one of the heart rate variability or the heart rate interval of the user indicates that the user is becoming drowsy.

The processor may be configured to determine that the heart rate variability is greater than or equal to a threshold amount or the heart rate interval is greater than or equal to a threshold interval. The threshold amount may be based on the stored baseline heart rate variability of the user. The threshold interval may be based on the stored baseline heart rate interval of the user. The processor may be configured to calculate a difference between the heart rate variability and the threshold amount or a difference between the heart rate interval and the threshold interval. The processor may be configured to activate the indicator based on at least one of the differences.

The drowsiness detection system may include a camera connected to the processor for detecting an identity of the user and a memory configured to store a baseline heart rate of the user. The processor may be configured to calculate a baseline heart rate variability and a baseline heart rate interval of the user based on the baseline heart rate. The processor may be configured to associate the identity of the user with the baseline heart rate of the user, the baseline heart rate interval and the baseline heart rate variability. The processor may be configured to store the association in the memory. The processor is configured to activate the indicator before the heart rate variability is greater than or equal to a threshold amount that indicates that the user is drowsy. The sensor may be connected or embedded within a wearable smart device and may be configured to remotely monitor and transmit the heart rate of the user to the processor.

In another aspect, the subject matter is embodied in a method for alerting a drowsy driver of a vehicle. The method includes obtaining, from a sensor by a processor, a heart rate of a user. The method includes measuring, by the processor, the heart rate of the user. The method includes calculating, by the processor, at least one of heart rate variability or a heart rate interval of the user based on the measured heart rate. The method includes determining, by the processor, that the at least one of the heart rate variability or the heart rate interval indicates that the user is potentially drowsy, and activating, by the processor, an indicator to the user.

In another aspect, the subject matter is embodied in a drowsiness detection system for a vehicle that includes a sensor configured to capture heart rate data. The drowsiness detection system includes a processor connected to the sensor. The processor is configured to determine a level of drowsiness of the user based on the heart rate data. The processor is configured to determine that the user is potentially drowsy before the level of drowsiness reaches or exceeds a threshold level where one or more symptoms of drowsiness are apparent to the user. The processor is configured to cause one or more adjustable vehicle components of the vehicle to activate to alert the user.

BRIEF DESCRIPTION OF THE DRAWINGS

Other systems, methods, features, and advantages of the present invention will be apparent to one skilled in the art upon examination of the following figures and detailed description. Component parts shown in the drawings are not necessarily to scale, and may be exaggerated to better illustrate the important features of the present invention.

DETAILED DESCRIPTION

Disclosed herein are systems, vehicles and methods for automatically predicting that a user is becoming drowsy and alerting the user before the drowsiness is recognizable. Particular embodiments of the subject matter described in this specification may be implemented to realize one or more of the following advantages.

A drowsiness detection system automatically predicts or determines that a user will be or is drowsy. The drowsiness detection system predictively alerts the user that he or she is drowsy so that the user, such as a driver of a vehicle, may take corrective action. By predictively detecting that a user will be or is drowsy, the drowsiness detection system alerts the user of his or her drowsiness before the drowsiness becomes apparent. This alert, for example, allows a driver to drive more safely and to take corrective action to prevent an accident. Moreover, this allows the driver to drive safely and to take a break more safely. Moreover, by predictively alerting the user that he or she will be drowsy before the drowsiness sets in, the drowsiness detection system allows the user to plan for breaks.

Other benefits and advantages include accounting for different users who have different abilities to cope with drowsiness. Additionally, the drowsiness detection system may account for different levels of drowsiness and may respond differently to the different levels of drowsiness. For example, the drowsiness detection system may have a visual indicator when a driver is slightly drowsy but output an audio indicator to wake the driver up when the driver is drowsier or does not respond to the visual indicator. In another example, the drowsiness detection system opens a window or the air conditioner to wake-up a dozing driver.

Figure 1:
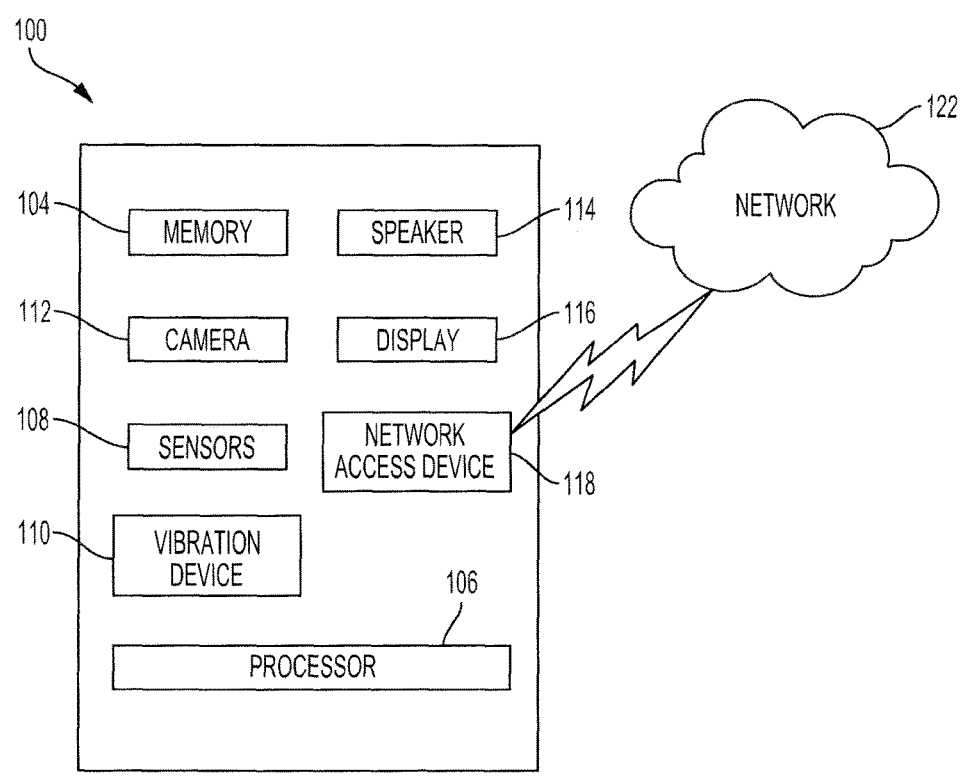
FIG. 1 is a block diagram of an example drowsiness detection system according to an aspect of the invention.
Figure 2:
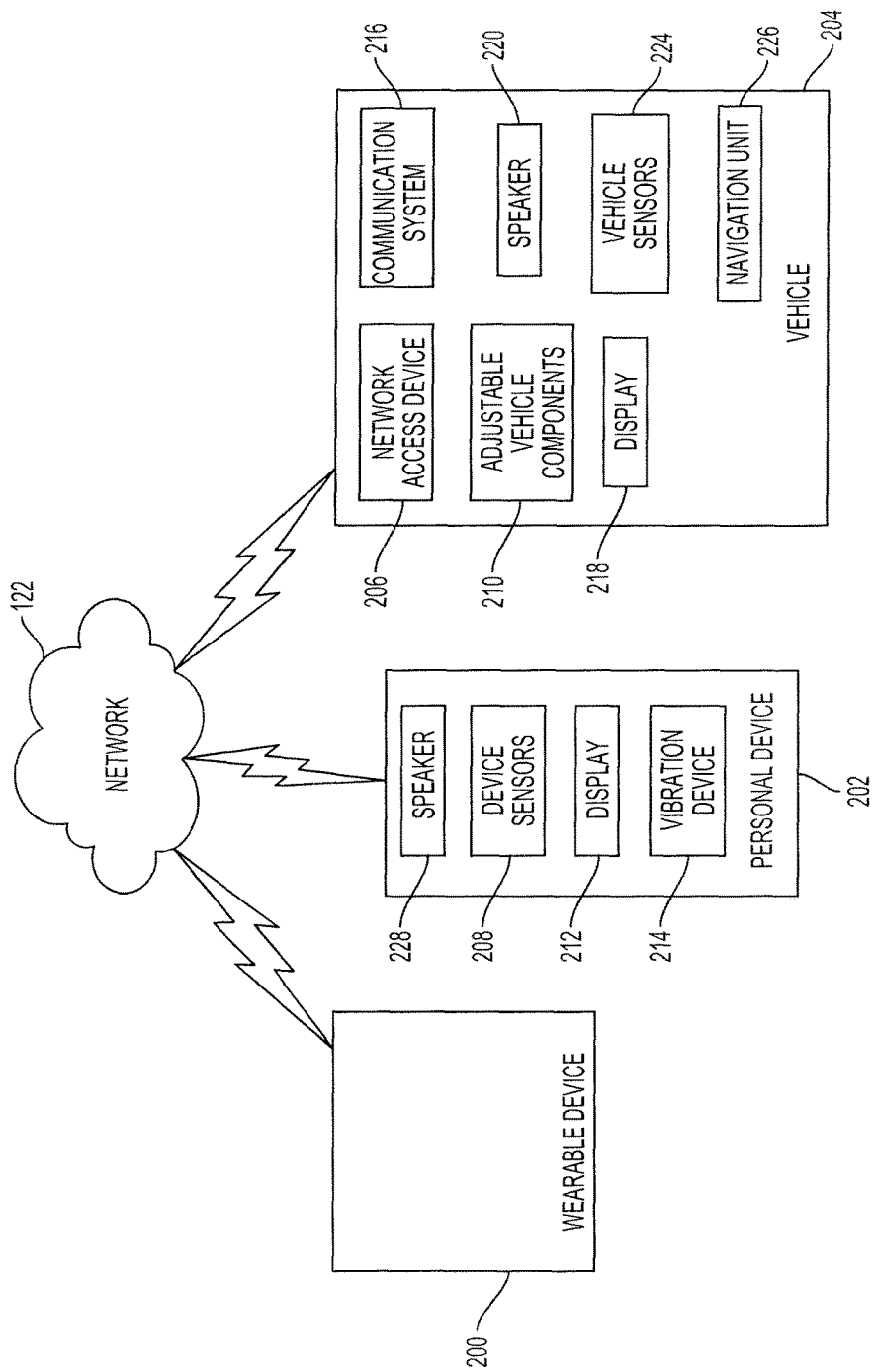
FIG. 2 is a block diagram of an example drowsiness detection system with a wearable device, a personal device and/or a vehicle according to an aspect of the invention.

FIG. 1 is a block diagram of an example drowsiness detection system 100. The drowsiness detection system 100 includes one of more computers or data processors 106, appropriately programmed, to detect and/or prevent drowsiness in a user before the user become drowsy. FIG. 2 is a block diagram of an example drowsiness detection system 100 embedded, integrated and/or connected within a wearable device 200, personal device 202 and/or a vehicle 204. When the drowsiness detection system 100 is in the personal device 202 and/or the vehicle 204, a wearable device 200 may obtain the heartbeat information and send the heartbeat information to the personal device 202 and/or the vehicle 204 via the wireless network, such as Bluetooth®. The drowsiness detection system 100 may be embedded within a wearable device 200, such as a smart watch. The wearable device 200 may be connected to the personal device 202. The drowsiness detection system 100 may be directly connected with the vehicle 204 and/or indirectly connected to the vehicle 204 through the personal device 202, such as a smartphone, tablet, laptop or other mobile device. The drowsiness detection system 100 may be connected to the vehicle 204 and/or the personal device 202 via network 122, such as a wireless network or a wired network. The vehicle 204 may have a network access device 206 that connects to the network access device 118 through the network 122. The drowsiness detection system 100 may be embedded within any of the wearable device 200, the personal device 202 or the vehicle 204.

A vehicle 204 is a conveyance capable of transporting a person, an object, or a permanently or temporarily affixed apparatus. A vehicle 204 may be a self-propelled wheeled conveyance, such as a car, sports utility vehicle, truck, bus, van or other motor or battery driven vehicle. For example, the vehicle 204 may be an electric vehicle, a hybrid vehicle, a plug-in hybrid vehicle or any other type of vehicle that includes a motor and/or generator. Other examples of vehicles include bicycles, trains, planes, or boats, and any other form of conveyance that is capable of transportation. The vehicle 204 may be semi-autonomous or autonomous. That is, the vehicle 204 may be self-maneuvering and navigate without human input. An autonomous vehicle may use one or more vehicle sensors 224 and/or navigation unit 226 to drive autonomously.

The vehicle 204 may be coupled to a network 122 through the network access device 206. The network 122, such as a local area network (LAN), a wide area network (WAN), a cellular network, a digital short-range communication (DSRC), the Internet, or a combination thereof, connects the vehicle 204, the personal device 202 and/or wearable device 200 that may have the drowsiness detection system 100 embedded within.

The drowsiness detection system 100 includes one or more processors 106, one or more sensors 108 and a memory 104. The drowsiness detection system 100 may include a speaker 114, a network access device 118, a camera 112, a display 116 and/or a vibration device 110.

The drowsiness detection system 100 may have a camera 112 or use a camera on the personal device 202 or vehicle 204 to capture image data. The drowsiness detection system 100 uses the image data to determine baseline heartbeat information. The one or more processors 106 may associate the identity of the user with the baseline heartbeat information and store the baseline heartbeat information into the memory 104.

The memory 104 may be coupled to the one or more processors 106. The memory 104 may store instructions to execute on the one or more processors 106 and may include one or more of a RAM or other volatile or non-volatile memory. The memory 104 may be a non-transitory memory or a data storage device, such as a hard disk drive, a solid-state disk drive, a hybrid disk drive, or other appropriate data storage, and may further store machine-readable instructions, which may be loaded and executed by the one or more processors 106. The memory 104 may store user profiles that include baseline heartbeat information of the user. The baseline heartbeat information includes a baseline heart rate, a baseline heart rate variability and/or a baseline heart rate interval of the user. The baseline heartbeat information is heartbeat information of the user that was previously recorded and/or measured over a previous time period.

Heart rate variability (HRV) is the variation in the time interval between heartbeats and is measured by the variation in the beat-to-beat interval. The heart rate variability is otherwise known as the cycle length variability, RR variability or heart period variability. The baseline heartbeat information may include other additional baseline heartbeat features.

The network access devices 118, 206 may include a communication port or channel, such as one or more of a Wi-Fi unit, a Bluetooth® unit, a Radio Frequency Identification (RFID) tag or reader, a DSRC unit, or a cellular network unit for accessing a cellular network (such as 3G or 4G). The network access device 118, 206 may transmit data to and receive data from the wearable device 200, the personal device 202 and/or the vehicle 204. For example, the drowsiness detection system 100 may be included in the wearable device 102 and communicate with the personal device 202 to activate an indicator and/or communicate with the vehicle 204 to activate an adjustable vehicle component 210.

The one or more sensors 108 may be coupled to the one or more processors 106 and include a heartbeat sensor. The heartbeat sensor detects the heart rate of the user. The heartbeat sensor may measure the heart rate of the user over a period of time, such as a minute. The drowsiness detection system 100 may be used to measure the heart rate of the user to calculate the heart rate variability (HRV), the heart rate interval and/or other additional heartbeat features. The personal device 202 and/or the vehicle 204 may have one or more device sensors 208 or vehicle sensors 224, respectively, that may remotely provide additional information, such as additional heartbeat information to the drowsiness detection system 100.

For example, the wearable device 102 may be positioned on the wrist of the user, such as a smart watch, and measure the pulse rate of the user at the user's wrist. In another example, the wearable device 102 may be a necklace and be positioned near the neck or heart to measure the pulse rate of the user.

The one or more vehicle sensors 224 may include a heartbeat sensor on the steering wheel that detects and/or measures the heart rate of the user when the user's hands are placed on the steering wheel. The one or more device sensors 208 may include a heartbeat sensor that measures and/or detects the heart rate of the user when positioned near the user's heart, such as in a shirt pocket, or have an accessory that is positioned near a user's wrist or neck. The one or more vehicle sensors 224 may include a proximity sensor to detect surrounding vehicles.

The drowsiness detection system 100 may have a display 116 that provides an interface to the user to provide visual notifications and/or alerts to the user. The drowsiness detection system 100 may have a speaker 114 to provide audio notifications and/or alerts to the user. The drowsiness detection system 100 may have a vibration device 110 to vibrate to notify and/or alert the user. The personal device 202 may have a vibration device 214, speaker 228 and/or a display 212. The vehicle 204 may have a display 218 and/or speaker 220. The drowsiness detection system 100 may cause the vibration device 214 of the personal device 202 to vibrate to alert the user or cause a notification to be displayed on the display 212, 218 or be outputted via the speaker 220, 228.

The vehicle 204 may have one or more adjustable vehicle components 210, such as a window, an entertainment center, a radio, a climate control system including an air conditioner (A/C) or heater, or other components that may be used to wake the user, such as a component that emits a smell. The one or more adjustable vehicle components 210 may have one or more settings, such as a fan level or temperature control for the climate control system. The vehicle 204 may have a communication system 216 that connects to the personal device 202 to receive and/or send a phone call, a short message service (SMS) message or use a message application to send a text.

The vehicle 204 may have a navigation unit 226 that may provide vehicle information and/or navigational map information. The navigation unit 226 may have or be connected to a Global Positioning System (GPS) device. The vehicle information may include the current position, location, direction of travel and/or speed of the vehicle 204. The navigational map information may include a route of the vehicle 204. The route includes an initial location or a current location of the vehicle 204, a destination and a path between the initial location or the current location and the destination. The vehicle 204 may use the one or more vehicle sensors 224 and the navigation unit 226 to navigate autonomously.

Figure 3:
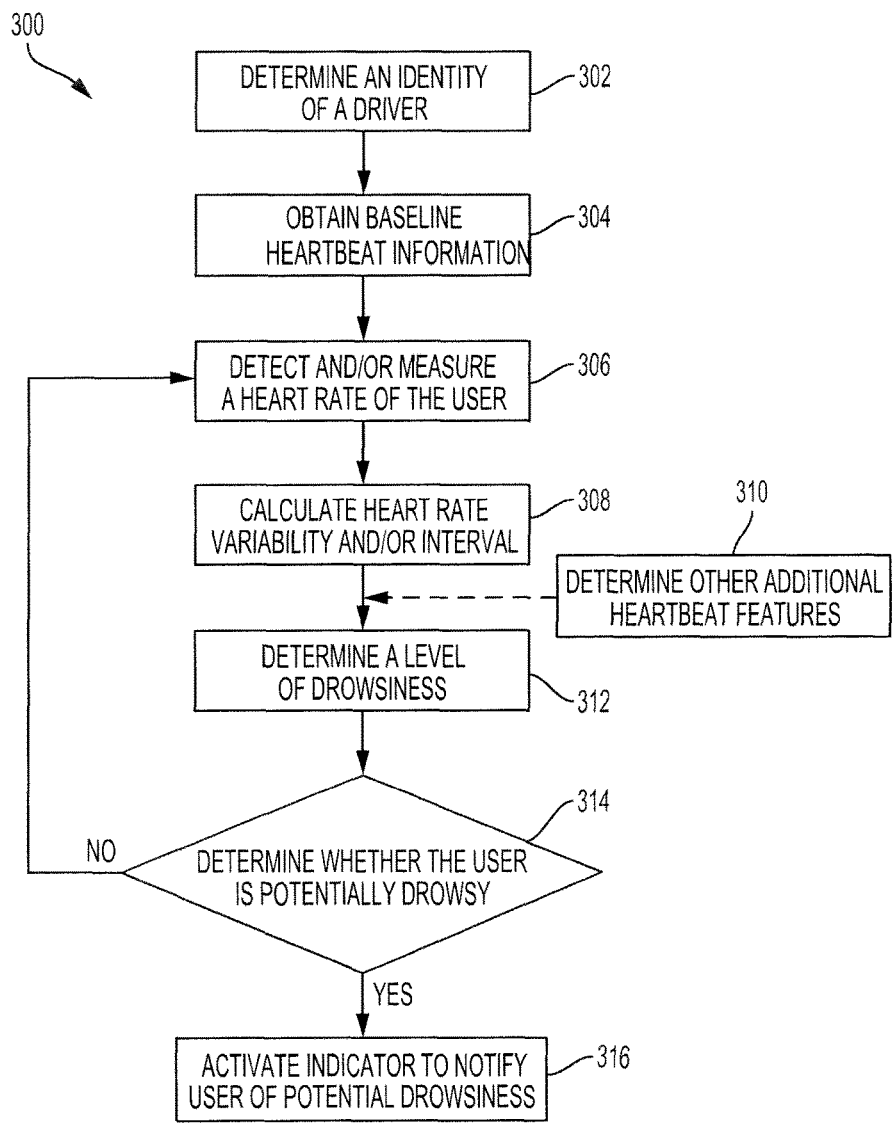
FIG. 3 is a flow diagram of an example process for detecting drowsiness in a user before the user becomes drowsy according to an aspect of the invention.

FIG. 3 is a flow diagram of an example process for detecting drowsiness in a user before the user becomes drowsy. One or more computers or one or more data processing apparatuses, for example, the one or more processors 106 of the drowsiness detection system 100 of FIG. 1, appropriately programmed, may implement the process 300.

The drowsiness detection system 100 may determine an identity of a driver during initialization (302). The drowsiness detection system 100 may receive user input, such as a user identification token, a user id or a fingerprint, which identifies the user, to determine the identity of the driver. For example, drowsiness detection system 100 may obtain a user id from the user, via a user interface, to identify the driver. The identity of the user may be associated with baseline heartbeat information and baseline breathing information that are stored in the memory 104.

The drowsiness detection system 100 may obtain or determine baseline heartbeat information (304). The memory 104 may have an internal database that associates the identity of the driver with previously stored baseline heartbeat information. The drowsiness detection system 100 may provide the identity of the driver to an internal database and receive the previously stored baseline heartbeat information associated with the identity of the driver. The baseline heartbeat information includes a baseline heart rate. The baseline heartbeat information may include a baseline heartbeat variability, a baseline heartbeat interval and/or other additional heartbeat features. In some implementations, the drowsiness detection system 100 calculates the baseline heartbeat variability, the baseline heartbeat interval and/or other additional heartbeat information after the drowsiness detection system 100 obtains the heart rate from the memory 104.

The drowsiness detection system 100 may determine the baseline heartbeat information and/or the baseline breathing information when the drowsiness detection system 100 initializes. When the drowsiness detection system 100 initializes, the drowsiness detection system 100 may collect the heartbeat information including the heart rate of the user over a period of time, such as a minute, and use the collected heartbeat information as the baseline heartbeat information.

The drowsiness detection system 100 detects and/or measures the heartbeat information of the user including a heart rate of the user (306). The drowsiness detection system 100 may detect and/or measure the heartbeat information of the user using one or more sensors 108, one or more device sensors 208 on a personal device 202 or one or more vehicle sensors 224 on the vehicle 204. The one or more sensors 108, the one or more device sensors 208 and/or the one or more vehicle sensors 224 may communicate to/from each other the heartbeat information and provide the heartbeat information to the one or more processors 106.

The drowsiness detection system 100 may measure the heart rate over a period of time, such as over a minute. The drowsiness detection system 100 may use the heart rate to calculate the heart rate variability (HRV) and/or the heartbeat interval (308). The drowsiness detection system 100 may measure the time between heartbeats and/or may calculate the heartbeat interval based on the heart rate of the user by calculating the inverse of the heart rate. The drowsiness detection system 100 may calculate the HRV based on the heart rate interval. The HRV is a measure of the variation in the time interval between the heartbeats. That is, the HRV is measured by the variation in the beat-to-beat interval.

The drowsiness detection system 100 may analyze, measure, detect and/or determine other additional heartbeat features based on the heart rate of the user (310). The other additional heartbeat features may include a frequency analysis of the RR interval, such as low frequencies of between approximately 0.04 Hz-0.15 Hz or high frequencies ranging from approximately 0.15 Hz-0.4 Hz. The other additional heartbeat features may include other statistical analysis of the RR interval, such as a calculation of the root-mean square standard deviation (RMSSD), i.e., the square root of the mean value of the square of differences between successively adjacent RRIs, the standard deviation, the Pnn50, i.e., the rate of RRI in which the difference between consecutive adjacent RRI exceeds 50 ms, the R-R Variance (RRV), and/or the number of peeks (RRI) over a period of time. These other additional heartbeat features may have corresponding baseline features stored in the memory 104.

Figure 4:
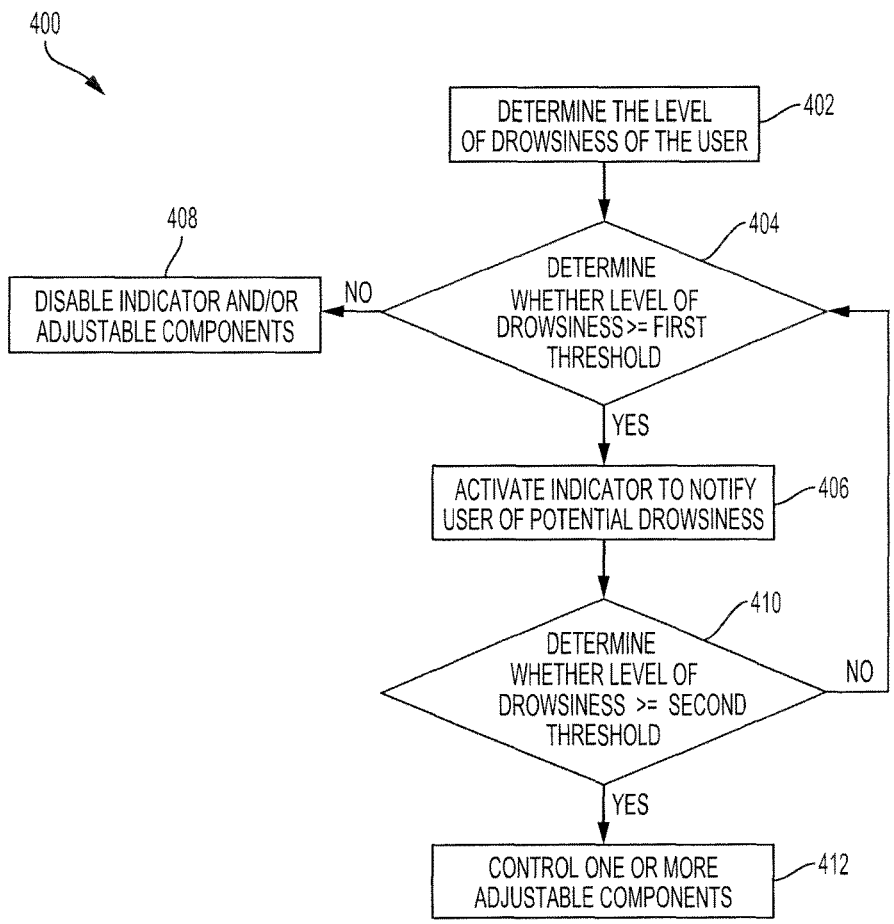
FIG. 4 is a flow diagram of an example process for alerting the user and activating one or more adjustable vehicle components to prevent the user from becoming drowsy according to an aspect of the invention.
Figure 5:
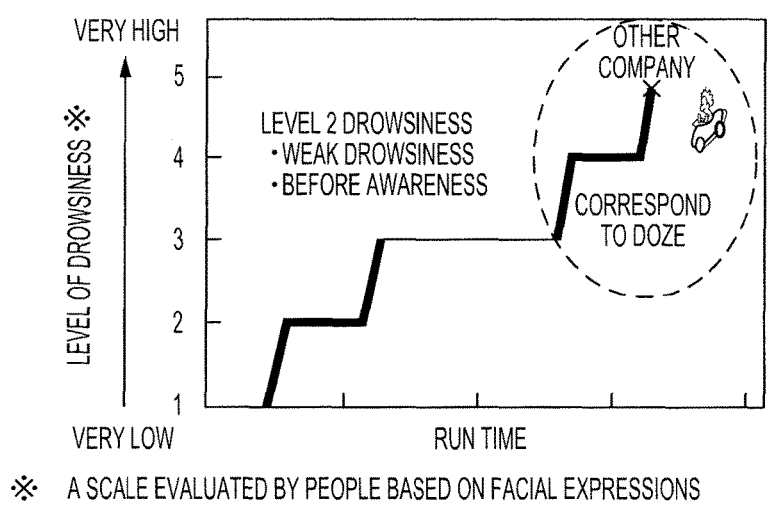
FIG. 5 is an example graphical illustration of the different stages of drowsiness of a user according to an aspect of the invention.

The drowsiness detection system 100 determines a level of drowsiness based on the heart rate variability, heartbeat interval and/or the other additional heartbeat features (312). The drowsiness detection system 100 may determine the level of drowsiness based on other models and/or other implementations. The other models and/or other implementations may be specialized to the individual or may be based on other individuals. The drowsiness detection system 100 may rate the potential drowsiness of the user on different levels, as shown in FIG. 5. Each level 1-5 corresponds to a level of drowsiness of the user on a scale evaluated by people based on facial expressions with level 1 indicating that the user has a low level of drowsiness or is alert and level 5 indicating that the user is dozing. As the levels increase from 1 to 5, the level of drowsiness increases. The levels increase from an awake state at level 1 to a low level of drowsiness or a weak drowsiness at level 3 where the user's drowsiness is unrecognizable, and finally, to a strong drowsiness at level 5 where the user is recognizably drowsy or dozing. FIG. 4 further describes a process 400 to determine the level of drowsiness.

The drowsiness detection system 100 determines whether the user is potentially drowsy before the user becomes drowsy based on the level of drowsiness (314). This potential drowsiness before the user becomes drowsy or becomes aware of his or her drowsiness may be a time when the user is mildly sleepy and desires some stimulation. For example, if the heartbeat interval is greater than or equal to a threshold interval or the HRV is greater than or equal to a threshold amount then the drowsiness detection system 100 may determine that the user is potentially drowsy which may overlap with a level 3 of drowsiness, as shown in FIG. 5. The threshold amount and/or the threshold interval may be approximately a threshold difference greater than or equal to the baseline heart rate variability and/or a threshold difference greater than or equal to the baseline heart rate interval, respectively. The threshold amount and/or the threshold interval may be within a range of the threshold amount and/or the threshold interval. The threshold difference may be a range.

The determination may be based on the level of drowsiness and/or the other additional heartbeat features. For example, an increase of the HF component or a high rate of RRI that indicates that a high rate of consecutive adjacent RRI exceeds 50 ms often and/or regularly may be related to a higher level of drowsiness in the user.

If the drowsiness detection system 100 determines that the user is not potentially drowsy, the drowsiness detection system 100 continues to monitor the heartbeat information of the user. If, however, the drowsiness detection system 100 determines that the user is potentially drowsy, the drowsiness detection system 100 may activate an indicator to notify the user of potential drowsiness or adjust the one or more adjustable vehicle components 210 of a vehicle 204 (316). For example, the drowsiness detection system 100 may notify the user by transmitting an audio indicator through one or more of the speakers 114, 228, 220. In another example, the drowsiness detection system 100 may alert the user on one or more of the displays 116, 212, 218. In another example, the drowsiness detection system 100 may activate a vibration device 110, 214 to alert the user of their potential drowsiness.

The drowsiness detection system 100 may activate the indicator, one or more adjustable vehicle components 210 and/or the communication system 216. The activation of the indicator, the one or more adjustable vehicle components 210 and/or the communication system 216 may be based on the level of drowsiness of the user. For example different levels of drowsiness may result in the activation of different components. FIG. 4 further describes a process 400 that controls the resulting indicator and/or the components based on the different levels of drowsiness.

FIG. 4 is a flow diagram of an example process 400 for alerting the user and activating one or more adjustable vehicle components 210 to prevent the user from becoming drowsy. One or more computers or one or more data processing apparatuses, for example, the one or more processors 106 of the drowsiness detection system 100 of FIG. 1, appropriately programmed, may implement the process 400.

The drowsiness detection system 100 may determine the levels of drowsiness of the user (402). The different levels of drowsiness range, for example, between levels 1 to 5, as shown in FIG. 5. The level 1 of drowsiness may be normalized to the baseline heartbeat information using the stored baseline heartbeat information so that the differences between the current and baseline heartbeat information correspond to the different levels. Each level of the different levels may correspond with a response by the drowsiness detection system 100 to prevent the user from entering a drowsiness state or awaken the user from the drowsiness state. That is, the corresponding response is designed to change the drowsiness level of the user by making the user more alert and less drowsy. The drowsiness detection system 100 may determine the level of drowsiness of the user based on the HRV, the heart rate interval and/or the other additional heartbeat features. The drowsiness detection system 100 may use a weighted combination of the factors to determine the level of drowsiness of the user.

The different levels of drowsiness correspond to the activity of autonomic nerve changes which correlate with the heartbeat information including the heart rate, the HRV, the heart rate interval and the other additional heartbeat features. The autonomic nerve changes are measured using a sympathetic number and a parasympathetic number which measure the sympathetic nervous system (SNS) and the parasympathetic nervous system (PSNS). The SNS stimulates the fight-or-flight response of the nervous system that reacts to stress or danger, whereas the PSNS activates the more tranquil functions of the body that occur when the body is at rest. The parasympathetic nerve becomes more active when an individual becomes sleepy without awareness. When the individual is aware of drowsiness and fighting drowsiness, the sympathetic nerve becomes active. When the sympathetic nerve becomes active, the heart rate variation and the heart beat interval decrease while the heart rate increases. When the parasympathetic nerve becomes active, heart rate variability and heart rate interval increase while the heart rate decreases.

The drowsiness detection system 100 may calculate a difference between the current HRV and the baseline HRV or threshold amount, the current heart rate interval and the baseline heart rate interval or threshold interval and/or the current values of the other additional heart features with the corresponding baseline information for the other additional heart features to determine the level of drowsiness of the user. The difference may be averaged over a period of time. For example, a larger difference between the current HRV and baseline HRV and/or current heart rate interval and baseline heart rate interval indicates a stronger level of drowsiness. Thus, as the difference between the current heart features and the baseline heart features increases, the user is more recognizably drowsy and the level of drowsiness increases from level 1 to 5. A larger heart rate interval in comparison to the baseline heart rate interval and/or a lower HRV in comparison to a baseline HRV indicates more drowsiness. The magnitude of the difference may be directly correlated to the level of drowsiness. Moreover, as the level of drowsiness increases, the sympathetic number of the user may gradually decrease as the level of activity in the autonomic nerve system including the SNS decreases.

The drowsiness detection system 100 may determine whether the level of drowsiness is greater than or equal to a first threshold level, e.g., the level 3 of drowsiness that indicates that the user is in a weak drowsiness state (404). The first threshold level may be a level of drowsiness that is unrecognizable by the user. That is, the first threshold level may be indicative that the user is potentially drowsy before the user is actually drowsy.

If the drowsiness detection system 100 determines that the level of drowsiness is greater than or equal to the first threshold value, the drowsiness detection system 100 may perform a first operation, such as activating an indicator to notify the user of the potential drowsiness or activation of an adjustable vehicle component 210 before the user becomes drowsy (406). Otherwise, if the level of drowsiness is less than the first threshold value or decreases below the first threshold value, the drowsiness detection system 100 may disable the first operation, such as deactivating the indicator and/or adjustable vehicle component 210 that notifies the user (408).

The drowsiness detection system 100 may determine whether the level of drowsiness is greater than or equal to a second threshold level, e.g., the level 5 of drowsiness indicates that the user is in a strong drowsiness state where the user is recognizably drowsy (410). That is, the second threshold level is greater than the first threshold level and may indicate that the user is drowsy and/or dozing. If the drowsiness detection system 100 determines that the level of drowsiness is greater than or equal to the second threshold value, the drowsiness detection system 100 may perform a second operation, such as controlling any number of the one or more adjustable vehicle components 210 or controlling the communication system 216 of the vehicle 204 (412). The activation of the first operation and/or the second operation may result in an increase in the sympathetic number of the user as the user is awaken from drowsiness and activity in the autonomic nerve system is increased which is reflected in the heartbeat information. The drowsiness detection system 100 may continue to monitor any changes in the level of drowsiness of the user and enable, disable and/or otherwise adjust the indicators and/or components based on the level of drowsiness.

For example, if the drowsiness detection system 100 determines that the level of drowsiness of the user is at level 3, the drowsiness detection system 100 may send an alert or notification to the display to indicate to the user of potential drowsiness. If the drowsiness detection system 100 determines that the level of drowsiness of the user increases to level 5, the drowsiness detection system 100 may cause one or more adjustable vehicle components 210 to activate. The one or more adjustable vehicle components 210 may include a window that opens when activated, a climate control system that activates the air conditioner or heater to alert the user, an entertainment center, such as a radio or a television, to turn on alert the user. In another example, the drowsiness detection system 100 may use a vehicle's communication system 216 to initiate a call from the personal device 202 to a specified individual so that the individual can converse with the user to keep the user alert. In another example, the drowsiness detection system 100 may use the personal device 202 to send an SMS message to another individual to alert them of the user's potential drowsiness so that the other individual can alert the user. The different types of activations of different operations may cause the user to awaken and their heartbeat and nerve activity to increase.

Exemplary embodiments of the methods/systems have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. A drowsiness detection system for a user, comprising:
a sensor configured to detect a heart rate of the user;
a plurality of indicators that when activated alert the user, the plurality of indicators including a first indicator and a second indicator; and
a processor connected to the sensor and configured to:
obtain the heart rate of the user;
measure the heart rate of the user;
calculate a heart rate variability or a heart rate interval of the user based on the measured heart rate;
calculate a difference between the heart rate variability and a baseline heart rate variability or a difference between the heart rate interval and a baseline heart rate interval;
determine that the user is at or within a first range of drowsiness for a first level of drowsiness or a second range of drowsiness for a second level of drowsiness based on the difference between the heart rate variability and the baseline heart rate variability or the difference between the heart rate interval and the baseline heart rate interval;
activate the first indicator to alert the user when the user is at or within the first range of drowsiness for the first level of drowsiness and the second indicator to alert the user when the user is at or within the second range of drowsiness for the second level of drowsiness, the first indicator being different than the second indicator; and deactivate the first indicator when the user is no longer at or within the first range of drowsiness and the second indicator when the user is no longer at or within the second range of drowsiness.

2. The drowsiness detection system of claim 1, further comprising:
a memory for storing a baseline heart rate of the user;
wherein to determine that the user is at or within the first range of drowsiness for the first level of drowsiness or the second range of drowsiness for the second level of drowsiness is further based on a comparison of the stored baseline heart rate with the measured heart rate of the user.

3. The drowsiness detection system of claim 1, wherein the difference between the heart rate variability and the baseline heart rate variability or the difference between the heart rate interval and the baseline heart rate interval is greater when the user is at or within the second range of drowsiness for the second level of drowsiness than when the user is at or within the first range of drowsiness for the first level of drowsiness.

4. The drowsiness detection system of claim 1, further comprising:
a camera connected to the processor for detecting an identity of the user; and
a memory configured to store a baseline heart rate of the user;
wherein the processor is configured to:
calculate the baseline heart rate variability and the baseline heart rate interval of the user based on the baseline heart rate of the user;
associate the identity of the user with the baseline heart rate of the user, the baseline heart rate interval of the user and the baseline heart rate variability; and
store the association in the memory.

5. The drowsiness detection system of claim 1, wherein the processor is configured to activate the first indicator before the difference between the heart rate variability and the baseline heart variability is greater than or equal to a threshold amount that indicates that the user is drowsy.

6. The drowsiness system of claim 1, wherein the sensor is connected or embedded within a wearable smart device and is configured to remotely monitor and transmit the heart rate of the user to the processor.

7. A method for alerting a user of a vehicle, comprising:
obtaining, from a sensor and by a processor, a heart rate of the user;
measuring, by the processor, the heart rate of the user;
calculating, by the processor, at least one of a heart rate variability or a heart rate interval of the user based on the measured heart rate;
determining, by the processor, that the user is at or within a first range of drowsiness for a first level of drowsiness or a second range of drowsiness for a second level of drowsiness based on a weighted combination of the heart rate of the user and the at least one of the heart rate variability or the heart rate interval;
activating, by the processor, a first indicator to alert the user when the user is at or within the first range of drowsiness for the first level of drowsiness and a second indicator to alert the user when the user is at or within the second range of drowsiness for the second level of drowsiness, the first indicator being different than the second indicator; and
deactivating, by the processor, the first indicator when the user is no longer at or within the first range of drowsiness and the second indicator when the user is at or within the second range of drowsiness.

8. The method of claim 7, further comprising:
storing, in a memory, a baseline heart rate of the user;
wherein determining that the user is at or within the first range of drowsiness for the first level of drowsiness or the second range of drowsiness for the second level of drowsiness based on the weighted combination of the heart rate of the user and the at least one of the heart rate variability or the heart rate interval includes comparing the stored baseline heart rate with the measured heart rate of the user.

9. The method of claim 7, wherein determining that the user is at or within the first range of drowsiness for the first level of drowsiness or the second range of drowsiness for the second level of drowsiness based on the weighted combination of the heart rate of the user and the at least one of the heart rate variability or the heart rate interval of the user includes determining that the heart rate variability is greater than or equal to a threshold amount or the heart rate interval is greater than or equal to a threshold interval.

10. The method of claim 9, wherein the threshold amount is based on a stored baseline heart rate variability of the user or the threshold interval is based on a stored baseline heart rate interval of the user.

11. The method of claim 7, further comprising:
detecting, by a camera, an identity of the user;
storing, in a memory, baseline heartbeat information including a baseline heart rate of the user;
calculating, by the processor, a baseline heart rate variability and a baseline heart rate interval of the user based on the baseline heart rate of the user;
associating the identity of the user with the baseline heart rate of the user, the baseline heart rate interval of the user and the baseline heart rate variability; and
storing, in the memory, the baseline heart rate interval, the baseline heart rate variability and the association.

12. The method of claim 7, wherein the first indicator is activated before the heart rate of the user is less than a threshold amount that indicates that the user is drowsy.

13. The method of claim 7, further comprising transmitting, by the sensor to the processor, the heart rate of the user.

14. A drowsiness detection system for a vehicle, comprising:
a sensor configured to capture heart rate data of a user including a heart rate variability and a heart rate interval; and
a processor connected to the sensor and configured to:
calculate a difference between the heart rate variability and a baseline heart rate variability or a difference between the heart rate interval and a baseline heart rate interval;
determine that the difference between the heart rate variability and the baseline heart rate variability or the difference between the heart rate interval and the baseline heart rate interval is within a first range that corresponds to a first level of drowsiness or within a second range that corresponds to a second level of drowsiness; and
activate a first adjustable vehicle component of the vehicle to alert the user when the difference between the heart rate variability and the baseline heart rate variability or the difference between the heart rate interval and the baseline heart rate interval is within the first range that corresponds to the first level of drowsiness and a second adjustable vehicle component to alert the user when the difference between the heart rate variability and the baseline heart rate variability or the difference between the heart rate interval and the baseline heart rate interval is within the second range that corresponds to the second level of drowsiness.

15. The drowsiness detection system of claim 14, wherein the heart rate data further includes at least one of a heart rate, a frequency analysis of the RRI, a square root of a mean value of the squares of differences between successively adjacent RRIs, a standard deviation of the heart rate, an R-R variance or a number of peaks of the RRI.

16. The drowsiness detection system of claim 14, wherein the second adjustable vehicle component is a communication device that connects to a personal device, wherein to activate the second adjustable vehicle component to alert the user the processor is configured to use the communication device to connect to and use the personal device to contact another device.

17. The drowsiness detection system of claim 14, further comprising a wearable smart device having one or more components, wherein the processor and the sensor are embedded within the wearable smart device.

18. The drowsiness detection system of claim 14, wherein a magnitude of the difference between the heart rate variability and the baseline heart rate variability or a magnitude of the difference between the heart rate interval and the baseline heart rate interval is directly correlated to a level of drowsiness.

* * * * *